United States Patent [19]

Winer et al.

[11] Patent Number: 4,592,909
[45] Date of Patent: Jun. 3, 1986

[54] WATER BASED DRINK FOR PEOPLE ENGAGED IN ATHLETIC OR OTHER STRENUOUS ACTIVITY

[75] Inventors: Steven Winer, Boston; William J. Evans, Cambridge, both of Mass.

[73] Assignee: Water Marketers, Inc., Boston, Mass.

[21] Appl. No.: 620,854

[22] Filed: Jun. 15, 1984

Related U.S. Application Data

[63] Continuation of Ser. No. 523,183, Aug. 15, 1983.

[51] Int. Cl.$^4$ ............... A61K 33/00; A61K 33/06; A61K 33/14; A61K 33/20
[52] U.S. Cl. .......................... 424/127; 424/149; 424/153; 424/154
[58] Field of Search ............... 424/127, 149, 154, 153

[56] References Cited

U.S. PATENT DOCUMENTS 3,657,424  4/1972  Atkins et al. .................. 424/149
4,322,407  8/1982  Ko ................................. 424/128

OTHER PUBLICATIONS

Physicians' Desk Reference (PDR) 1974—p. 980, Quarterly Supp. 7-66, p. 31.

Primary Examiner—Stanley J. Friedman
Attorney, Agent, or Firm—Thompson, Birch, Gauthier & Samuels

[57] ABSTRACT

A water based drink formulated for consumption by people engaged in athletic or other strenuous activity is disclosed. The drink comprises purified water to which has been added electrolytes (ions) of the type normally lost in such activity and in amounts in proportion to which the electrolytes are normally lost. The drink does not include sugar which increases osmolarity and retards gastric emptying. The drink may consist essentially combinations of purified water, sodium chloride, sodium phosphate, potassium chloride, potassium phosphate, calcium chloride and magnesium chloride with the salts being proportioned as stated.

2 Claims, No Drawings

WATER BASED DRINK FOR PEOPLE ENGAGED IN ATHLETIC OR OTHER STRENUOUS ACTIVITY

This is a continuation of application Ser. No. 523,183 filed Aug. 15, 1983.

BACKGROUND OF THE INVENTION

The present invention relates generally to water based drinks and more particularly to a water based drink that is formulated especially for people engaged in physical or other strenuous activity.

Physical activity places a great metabolic demand on the human body. One of the important by-products of exercise is increased heat production. Blood flow through exercising muscles may increase to 15 to 20 times the resting level allowing this heat to diffuse from the muscle cell and warm the blood. The exchange of heat between the body and the environment requires that it be transported from the core to the periphery via an augmetation of cutaneous blood flow, by the process of vasodilation. The blood vessels directly below the skin open up and allow blood to circulate near the surface of the body. This acts as a radiation of sorts by bringing the heat to the surface to be dissipated, with the cooler blood returning to the muscles to again be warmed. Heat loss from the skin occurs through conduction, convection (radiation to the environment), or through the evaporation of sweat. During exercise, sweat evaporation is the greatest avenue for heat dissipation.

Loss of sweat from the body is an important physiological consideration. Sweat is hypotonic, that is, it has a lower concentration of salts and other solutes than does blood. Profuse sweating causes excessive loss of body water. This leads to a decrease in sweating rate and less evaporative cooling. Decreased blood volume can lead to a circulatory collapse and decreased evaporative cooling can cause an excessive rise in body temperature. Clinical problems in athletes exposed to environmental heat can vary from temporary heat cramps to fatal heat stroke.

The main problem therefore, in exposure to environmental heat is water loss. The well-hydrated athlete is a more efficient and effective athlete. It is of primary importance that everthing be done to provide adequate hydration before, during, and after all sporting events and other types of strenuous activity.

For example, in football, a 250 lb. athlete may lose as much as 10 lb. or 5 quarts of water in a 90 minute practice. Water is a nutrient critical to athletic performance and is certain situations is critical to the athlete's safety.

A number of different water based drinks formulated especially for persons engaged in strenuous activity are presently being marketed. One of the problems with these drinks, however, is that they all contain sugar. Actually, there is no need for sugar in an athletic drink. Sugar in solutions has been shown to have a potentially detrimental effect on performance. It can severely limit the rate of gastric emptying. Sugar (glucose or sucrose), when consumed before exercise, can actually cause hypoglycemia (low blood sugar) during exercise.

Obviously, rapid fluid replacement is the primary objective for athletes during competition and for anyone engaging in strenuous physical activity on a hot day. The biggest factor which determines the stomach's emptying rate appears to be the osmolarity of the solution. Osmolarity is defined as the number of dissolved particles in a water solution. It has been found that the osmolarity most ideal for emptying the stomach is around 200 to 210 m Osm per liter or lower. As far as is known, that is substantially less than most commercial products available of this type, which means that all the products will tend to empty more slowly from the stomach and consequently will be more filling for the individual who has to rehydrate rapidly.

U.S. Pat. No. 3,375,913 discloses a water vending machine in which a predetermined quantity of minerals is added to demineralized water to make the water suitable for drinking and/or beneficial to the human system, the minerals including chlorides and sulfates of calcium, magnesium and sodium, soluble salts of other minerals such as iron and manganese and fluorides.

Accordingly, it is an object of this invention to provide a new and improved drink.

It is another object of this invention to provide a water based drink which is especially formulated for people engaged in athletic or other strenuous activity.

It is still another object of this invention to provide a water based drink which is especially formulated for people engaged in strenuous activity that does not include sugar, and for those who must limit the intake of sugar.

It is a further object of this invention to provide a water based drink which includes electrolytes normally lost in strenuous activity.

It is still a further object of this invention to provide a water based drink which includes electrolytes normally lost in strenuous activity and in the amounts in which said electrolytes are normally lost.

It is yet still a further object of this invention to provide a water based drink which has a low osmolarity.

SUMMARY OF THE INVENTION

A water based drink especially formulated for people engaged in physical or other strenuous activity according to the teachings of the present invention consists essentially of purified water, sodium chloride or phosphate, potassium chloride or phosphate, calcium chloride and magnesium chloride, the sodium, potassium, calcium chloride and magnesium being in amounts in porportion to which they are normally lost by a person during athletic or other strenuous activity.

Various objects and advantages will appear from the description to follow. In the description, reference is made to the accompanying examples which forms a part thereof, and in which is shown by way of illustration, a specific embodiment for practicing the invention. This embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appending claims.

DETAILED DESCRIPTION OF THE INVENTION

The present invention is based on the realization that (1) there is no need for sugar in an athletic drink, and in fact, sugar is an undesirable element, (2) the most important electrolytes lost during physical or other strenuous activity are sodium, potassium, calcium chloride and magnesium, (3) the proportions in which the electrolytes are lost are as follows: (a) sodium from about 5 meq/L to about 148 meq/L, (b) potassium from about 1 meq/L to about 15 meq/L, (c) calcium from about 1 to 8 meq/L and (d) magnesium from about 0.04 to 0.4 and (e) chlorides from about 2.000 to about 2.62 meq/L and (4) an ideal drink for persons engaged in athletic or other physical activity is one providing rapid fluid replacement and containing these electrolytes in the above proportions and having an osmolarity of about 200 to 210 m Osm. per liter or lower and no sugar.

Preferred compositions of the drink typically comprise from about 0.006 to about 0.010% by weight of sodium chloride, from about 0.0045 to about 0.0075% by weight of potassium chloride, from about 0.000192 to about 0.000312% by weight of magnesium chloride from about 0.00375 to about 0.00625% by weight of calcium chloride and the balance purified water. Instead of potassium chloride the composition may from about 0.0065 to about 0.0109% by weight of potassium phosphate and instead of sodium chloride the composition may comprise from about 0.00900 to about 0.001500% by weight of sodium phosphate. The purified water contains less than around 10 parts per million of dissolved minerals.

The following examples are intended to illustrate the present invention, and should not be construed as limitative, the scope of the invention being determined by the appended claims:

EXAMPLE I

| Ingredient | Percent by weight |
| --- | --- |
| Sodium chloride | .008 |
| Potassium chloride | .0087 |
| Calcium chloride dehydrate | .005 |
| Magnesium chloride | .00025 |
| Purified water | Balance |

The osmolarity of the sodium chloride, potassium chloride, calcium chloride and magnesium chloride is about 30MOsm/L

EXAMPLE II (concentrated form)

| Ingredient | Percent by weight |
| --- | --- |
| Sodium chloride | 4 |
| Potassium chloride | 4.35 |
| Calcium chloride dehydrate | 5 |
| Magnesium chloride | .25 |
| Purified water | Balance |

EXAMPLE III

| Ingredient | Percent by weight |
| --- | --- |
| Sodium chloride | .006 |
| Potassium chloride | .0045 |
| Calcium chloride dehydrate | .00375 |
| Magnesium chloride | .000192 |
| Purified water | Balance |

EXAMPLE IV

| Ingredient | Percent by weight |
| --- | --- |
| Sodium chloride | .010 |
| Potassium chloride | .0075 |
| Calcium chloride dehydrate | .00613 |
| Magnesium chloride | .000312 |
| Purified water | Balance |

EXAMPLE V

| Ingredient | Percent by weight |
| --- | --- |
| Sodium chloride | .008 |
| Potassium phosphate | .0065 |
| Calcium chloride dehydrate | .005 |
| Magnesium chloride | .00025 |
| Purified water | Balance |

EXAMPLE VI

| Ingredient | Percent by weight |
| --- | --- |
| Sodium chloride | .008 |
| Potassium phosphate | .0109 |
| Calcium chloride dehydrate | .005 |
| Magnesium chloride | .00025 |
| Purified water | Balance |

EXAMPLE VII

| Ingredient | Percent by weight |
| --- | --- |
| Sodium phosphate | .009 |
| Potassium chloride | .0087 |
| Calcium chloride dehydrate | .005 |
| Magnesium chloride | .00025 |
| Purified water | Balance |

EXAMPLE VIII

| Ingredient | Percent by weight |
| --- | --- |
| Sodium phosphate | .001500 |
| Potassium chloride | .0087 |
| Calcium chloride dehydrate | .005 |
| Magnesium chloride | .0025 |
| Purified water | Balance |

The embodiment of the present invention is intended to be merely exemplary and those skilled in the art shall be able to make numerous variations and modifications to it without departing from the spirit of the present invention. All such variations and modifications are intended to be within the scope of the present invention as defined in the appended claims.

EXAMPLE IX

| Ingredient | Percent by weight |
| --- | --- |
| Sodium chloride | .0040 |
| Sodium phosphate | .0040 |
| Potassium chloride | .0110 |
| Calcium chloride | .00370 |
| Magnesium chloride | .00020 |

EXAMPLE X

| | |
|---|---|
| Sodium chloride | .010 |
| Potassium chloride | .011 |
| Calcium chloride | .0062 |
| Magnesium chloride | .00025 |

What is claimed is:

1. A fluid replacement drink for rapidly restoring bodily fluids and rapidly replacing physiologically important electrolytes in the proportions which they are lost during strenuous physical activity, consisting essentially of:

a. from about 0.006 to about 0.010 wt.% sodium chloride or from about 0.00900 to about 0.00150 wt.% sodium phosphate;

b. from about 0.0045 to about 0.0075 wt.% potassium chloride or from about 0.065 to about 0.0109 wt.% potassium phosphate;

c. from about 0.00375 to about 0.00613 wt.% calcium chloride; and d. from about 0.000912 to about 0.000312 wt.% magnesium chloride; and e. purified water; said electrolytes combined in an effective amount such that the osmolarity of said drink is not more than approximately 50–80 m. osm. per liter to ensure that the stomach is emptied of fluid and electrolytes at a controlled rate.

2. A drink as defined in claim 1 wherein effective amounts of sodium chloride and sodium phosphate are used in combination.

* * * * *